United States Patent [19]

Edwards

[11] 4,160,845
[45] Jul. 10, 1979

[54] FUNGICIDAL N-(HALOALIPHATICTHIO)HALOVINYL-SULFONAMIDES

[75] Inventor: Laroy H. Edwards, Napa, Calif.

[73] Assignee: Chevron Research Company, San Francisco, Calif.

[21] Appl. No.: 646,134

[22] Filed: Jan. 2, 1976

[51] Int. Cl.² .................. A01A 9/00; C07C 143/822
[52] U.S. Cl. ........................ 424/298; 260/453 RW
[58] Field of Search ................ 260/453 R, 453 RW; 424/298

[56] References Cited

U.S. PATENT DOCUMENTS

| 2,844,628 | 7/1958 | Kuhle et al. | 260/453 RW |
| 3,178,447 | 4/1965 | Kohn | 260/453 RW |
| 3,555,055 | 1/1971 | Kaplan | 260/453 RW |
| 3,678,017 | 7/1972 | Shelton et al. | 260/453 RW |
| 3,703,500 | 11/1972 | Nast et al. | 260/453 RW |
| 3,915,940 | 10/1975 | Vander Kooi | 260/453 R |

FOREIGN PATENT DOCUMENTS 2094444  6/1970  France ................. 260/453 R

*Primary Examiner*—Delbert R. Phillips
*Attorney, Agent, or Firm*—Dix A. Newell; T. G. DeJonghe

[57] ABSTRACT

Novel sulfonamides of the formula

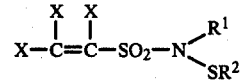

wherein $R^1$ is alkyl, cycloalkyl or aryl; $R^2$ is haloalkyl or halovinyl; and X is hydrogen or halogen and at least one X is halogen, are useful for the prevention or cure of fungal infections.

9 Claims, No Drawings

FUNGICIDAL N-(HALOALIPHATICTHIO)HALOVINYLSULFONAMIDES

DESCRIPTION OF THE PRIOR ART

U.S. Pat. No. 3,178,447, issued Apr. 13, 1965 to G. K. Kohn, discloses pesticidal N-(haloalkylthio)alkyl- and N-(haloalkylthio)aryl sulfonamides. French Pat. No. 2,094,444, published Feb. 4, 1972, of Products Chimiques Pechiney Saint Gobain, discloses the use of trichlorovinylsulfonamide as a bactericide and fungicide.

DESCRIPTION OF THE INVENTION

The sulfonamides of the invention are represented by the formula

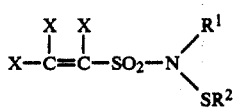

wherein $R^1$ is alkyl of 1 to 6 carbon atoms, cycloalkyl of 3 to 8 carbon atoms, phenyl substituted with up to 2 (0 to 2) of the same or different substituents selected from trifluoromethyl, trichloromethyl, fluoro, chloro, bromo, nitro or alkyl of 1 to 4 carbon atoms; $R^2$ is haloalkyl of 1 to 3 carbon atoms and 1 to 7 of the same or different halogens selected from fluoro, chloro or bromo or halovinyl of 1 to 3 of the same or different halogens selected from fluoro, chloro or bromo; and the X groups are the same or different and are hydrogen, fluoro, lower alkyl of 1 to 6 carbon atoms, chloro, bromo or iodo, with the proviso that at least one X is halogen.

Representative alkyl $R^1$ groups are methyl, ethyl, propyl, isopropyl, butyl and hexyl. Representative cycloalkyl $R^1$ groups are cyclopropyl, cyclobutyl, cyclopentyl and cyclooctyl. Representative substituted phenyl $R^1$ groups are o-trifluoromethylphenyl, m-trifluoromethylphenyl, p-trichloromethylphenyl, o-fluorophenyl, m-chlorophenyl, p-bromophenyl, 2,4-dichlorophenyl, 3,5-dibromophenyl, 3-bromo-4-chlorophenyl, o-tolyl, 2,4-dimethylphenyl, p-nitrophenyl and 2-chloro-4-methylphenyl. Representative haloalkyl $R^2$ groups are chloromethyl, trifluoromethyl, dichloromethyl, trichloromethyl, fluorodichloromethyl, tribromoethyl, 2,2,2-trichloroethyl, 1,2,2,2-tetrachloroethyl, 1,1,2,2-tetrabromoethyl, pentachloroethyl, 2,2,3,3,3-pentabromopropyl and 3,3,3-trichloropropyl. Representative halovinyl $R^2$ groups are 1-chlorovinyl, 2,2-difluorovinyl, 1,2-dibromovinyl, trichlorovinyl and tribromovinyl.

The preferred X groups are chloro or bromo. The preferred $R^1$ group is lower alkyl of 1 to 3 carbon atoms, cycloalkyl of 5 to 6 carbon atoms, phenyl or phenyl substituted with 1 or 2 fluoro, chloro, bromo or alkyl of 1 to 4 carbon atoms. The preferred $R^2$ group is polyhaloalkyl of 1 to 2 carbon atoms and 2 to 5 of the same or different halogens selected from chloro or bromo, especially trichloromethyl and tetrachloroethyl.

A preferred class of sulfonamides of formula (I) is that wherein the X groups are the same and are chloro or bromo, $R^1$ is alkyl of 1 to 3 carbon atoms, and $R^2$ is polyhaloalkyl of 1 to 2 carbon atoms and 2 to 5 of the same or different halogens selected from chloro or bromo.

Another preferred class of sulfonamides of formula (I) is that wherein the X groups are the same and are chloro or bromo, $R^1$ is cycloalkyl of 5 to 6 carbon atoms and $R^2$ is polyhaloalkyl of 1 to 2 carbon atoms and 2 to 5 of the same or different halogens selected from chloro or bromo.

Representative sulfonamides of formula (I) are:

N-ethyl-N-(1,2,2,2-tetrachloroethylthio)-1-chlorovinylsulfonamide,
N-cyclopentyl-N-(perchloropropylthio)-2-bromovinylsulfonamide;
N-(3,4-dichlorophenyl)-N-(tribromomethylthio)-1-chloro-2-bromovinylsulfonamide,
N-methyl-N-(trichlorovinylthio)-1,2-dichloroallylsulfonamide,
N-methyl-N-(chloromethylthio)trifluorovinylsulfonamide and
N-p-tolyl-N-(difluoromethyl)tribromovinylsulfonamide.

The sulfonamides of the invention are prepared by reacting a halovinylsulfonyl chloride (II) with an amine or aniline compound (III), and sulfenylating the resulting halovinylsulfonamide (IV) with a sulfenyl halide (V) in the presence of an acid acceptor. These reactions are depicted in reactions (1) and (2):

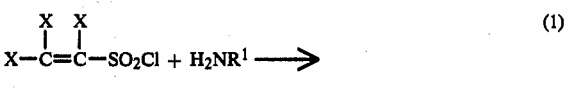

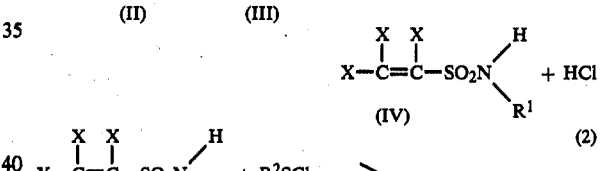

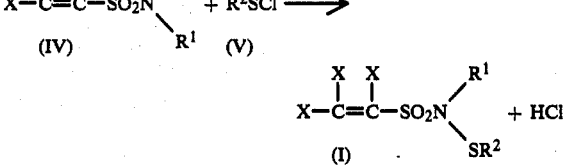

wherein $R^1$, $R^2$ and X have the same significance as previously defined.

Reaction (1) is conducted by reacting substantially equimolar quantities of the sulfonyl chloride (II) and the amine or aniline (III) in an inert diluent at a temperature of 0° to 100° C. If desired, a molar excess of the amine or aniline (III), or an acid acceptor as defined below, can be used as an acid acceptor for the hydrogen chloride produced in the reaction. Reaction (2) is conducted by reacting substantially equimolar quantities of the sulfonamide (IV) and the sulfenyl halide (V) in the presence of an acid acceptor. Suitable acid acceptors are organic amines such as pyridine compounds, e.g., pyridine or alpha-picoline, and lower trialkylamines, e.g., triethylamine or tripropylamine. Generally, at least one mol of acid acceptor is employed for each mol of sulfenyl halide. The reaction is normally conducted in an inert liquid diluent, e.g., organic solvents such as chlorinated hydrocarbons. The product (I) is isolated and purified by conventional procedures such as extraction, filtration, crystallization and chromatography.

The halovinylsulfonyl chloride reactant (II) may be prepared by reacting a bis-halovinyl disulfide with an aqueous chlorine solution in the liquid phase at a temperature of 0° to 50° C.

The compounds of the invention are useful for controlling fungi, particularly plant fungal infections caused by *Botrytis cinerea*, leaf blights caused by organismis such as *Septoria apii*, *Alternaria solani conidia* and *Phytophthora infestans conidia*, powdery mildew caused by organisms such as *Erysiphe polygoni* and *E. chicoraciarum*, and other fungal infections caused by organisms such as *Pythrium ultimum*, *Helminthosporum sativum*, *Fusarium moniliforme*, *Rhizoctonia solani*, *Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divide particles which disperse readily in water or other dispersant. These compositions normally contain from about 5-80% fungicide, and the rest inert material, which includes dispersing agents, emulsifying agents, and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier, such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of these these techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

EXAMPLE 1

Preparation of trichlorovinylsulfonyl chloride

Chlorine (80.0 g, 1.1 mol) was bubbled into a stirred solution of 32.5 g (0.1 mol) bis-trichlorovinyl disulfide and 7.2 g (0.4 mol) water in 50 cc glacial acetic acid. The temperature was maintained at 5°-15° C. during the chlorine addition with an ice bath. After the chlorine addition was completed, the homogeneous reaction solution was warmed to about 25° C. and stirred until hydrogen chloride gas evolution ceased. The reaction solution was then distilled through a short column to give 25 g (55% yield) of trichlorovinylsulfonyl chloride, b.p. 45° C. at 0.05 mm of Hg (70°-75° C. at 3.1 mm of Hg).

EXAMPLE 2

Preparation of N-(p-chlorophenyl)trichlorovinylsulfonamide

A solution of 7.6 g (0.06 mol) p-chloroaniline and 7.0 g (0.03 mol) trichlorovinylsulfonyl chloride in 150 ml chloroform was heated under reflux for 3 hours. The reaction mixture was then cooled, washed with water, dried over magnesium sulfate and evaporated to give an oily residue. The residue was chromatographed on silica gel. N-(p-chlorophenyl)trichlorovinylsulfonamide, m.p. 73°-76° C., was eluted from the silica gel with 30% ether-70% hexane. Elemental analysis for $C_8H_5Cl_4NO_2S$ showed: calculated, %S, 9.99, %Cl 44.2; found, %S, 10.1, %Cl 48.2.

EXAMPLE 3

Preparation of N-methyl-N-(trichloromethylthio)trichlorovinylsulfonamide

A 2.8 g (0.0312 mol) sample of tichlorovinylsulfenyl chloride was added in one portion to a cooled (−10° C.) solution of 7.0 g (0.312 mol) N-methyltrichlorovinylsulfonamide in 150 ml dichloromethane. A 4.0 g (0.04 mol) sample of triethylamine was then added dropwise to the cooled solution. The resulting reaction sultion was allowed to warm to about 25° C. and stirred for about 2 hours. The reaction mixture was washed with water, dried over magnesium sulfate and evaporated to give an oil. The oil was crystallized from hexane to give 5.5 g (47% yield) of N-methyl-N-(trichloromethylthio)trichlorovinylsulfonamide, m.p. 57°–58° C. The elemental analysis for the product is tabulated in Table I under Compound No. 1.

EXAMPLE 4

Preparation of N-cyclohexyl-N-(1,1,2,2-tetrachloroethylthio)trichlorovinylsulfonamide A 4.0 g (0.04 mol) sample of triethylamine was added dropwise to a cooled (−10° to 0° C.) solution of 9.5 g (0.0324 mol) N-(cyclohexyl)trichlorovinylsulfonamide, m.p. 152°–153° C., and 7.6 g (0.0324 mol) 1,1,2,2-tetrachloroethylsulfenyl chloride in 200 ml dichloromethane. The reaction mixture was then stirred at about 25° C. for 3 hours, washed with water, dried over magnesium sulfate and evaporated to give an oil. The oil was chromatographed on silica gel. The N-cyclohexyl-N-(1,1,2,2-tetrachloroethylthio)trichlorovinylsulfonamide product, 11 g (72% yield), was eluted from the silica gel with 30% ether/20% hexane. The infrared spectrum of the product showed strong absorption bands at 1385 $cm^{-1}$ and 1160 $cm^{-1}$. The elemental analysis for the product is tabulated in Table I under Compound No. 6.

EXAMPLE 5

Preparation of N-phenyl-N-(trichloromethythio)trichlorovinylsulfonamide

A 2.2 g (0.022 mol) sample of triethylamine was added dropwise to a cooled (−10° C.) solution of 5.0 g (0.015 mol) trichloromethylsulfenyl chloride in 150 ml dichloromethane. The reaction mixture was then warmed to about 25° C., stirred for 2 hours, washed with water, dried over magnesium sulfate and evaporated to give an oil. The oil was chromatographed on silica gel. The N-phenyl-N-(trichloromethylthio)trichlorovinylsulfonamide product was eluted from the silica gel with 30% ether-70% hexane. The infrared spectrum of the product showed strong absorption bands at 1700 $cm^{-1}$, 1395 $cm^{-1}$ and 1180 $cm^{-1}$. The elemental analysis is tabulated in Table I under Compound No. 7.

The compounds tabulated in Table I were prepared by procedures similar to those described in Examples 2-5.

EXAMPLE 6

Mycelial Inhibition

The compounds of the present invention were evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were inoculated with the particular mycelium growth by convering the paper with a potato dextrose broth culture of mycelial suspension. The inoculated papers were then placed on potato dextrose agar plates and sprayed by means of a microsprayer with the fungicidal solution. The treated paper strips were incubated at 25° C. and data were taken after 24 hours. Fungicidal activities were measured by a zone of inhibited mycelial growth from the center of the paper strip. The effectiveness of the compounds tested for fungicidal activity is reported in Table II in terms of the micrograms/$cm^2$ for 99% control of the fungus.

TABLE I

Compounds of the formula $Cl_2C=CClSO_2N\begin{smallmatrix}R^1\\R^3\end{smallmatrix}$

| Compound No. | $R^1$ | $R^3$ | Melting Point, °C. | Sulfur Calc. | Sulfur Found | Chlorine Calc. | Chlorine Found |
|---|---|---|---|---|---|---|---|
| 1 | $CH_3$ | $SCCl_3$ | 57–58 | 17.2 | 17.3 | 56.9 | 55.2 |
| 2 | $CH_3$ | $SCCl_2CCl_2H$ | oil | 15.2 | 15.3 | 58.8 | 58.6 |
| 3 | i-$C_3H_7$ | $SCCl_2CCl_2H$ | 65–67 | 14.2 | 14.3 | 55.1 | 54.2 |
| 4 | i-$C_3H_7$ | $SCCl_3$ | 88–90 | 16.0 | 15.9 | 52.9 | 52.9 |
| 5 | cyclohexyl | $SCCl_3$ | oil | 14.5 | 14.9 | 48.1 | 49.8 |
| 6 | cyclohexyl | $SCCl_2CCl_2H$ | oil | 13.1 | 13.3 | 50.6 | 48.7 |
| 7 | φ | $SCCl_3$ | oil | 14.7 | 14.5 | 48.8 | 45.7 |
| 8 | φ | $SCCl_2CCl_2H$ | oil | 13.2 | 13.1 | 51.2 | 49.3 |
| 9 | 2,6-$(CH_3)_2$-φ | $SCCl_3$ | oil | 13.8 | 12.9 | 45.8 | 43.0 |
| 10 | 2,6-$(CH_3)_2$-φ | $SCCl_2CCl_2H$ | 107–108 | 12.5 | 12.3 | 48.4 | 46.2 |
| 11 | 4-$CH_3$-φ | $SCCl_3$ | 73–75 | 14.3 | 13.5 | 47.3 | 46.9 |
| 12 | 4-$CH_3$-φ | $SCCl_2CCl_2H$ | oil | 12.9 | 12.2 | 49.8 | 44.6 |
| 13 | $CH_3$ | H | oil | 14.3 | 13.8 | 47.4 | 43.0 |
| 14 | i-$C_3H_7$ | H | oil | 12.7 | 12.4 | 42.1 | 43.6 |
| 15 | cyclohexyl | H | oil | 11.0 | 10.4 | 36.4 | 35.3 |
| 16 | φ | H | oil | 11.2 | 10.9 | 37.1 | 35.9 |
| 17 | 2,6-$(CH_3)_2$-φ | H | 127–128 | 10.2 | 9.9 | 33.8 | 32.3 |
| 18 | 4-$CH_3$-φ | H | 95–97 | 10.7 | 10.5 | 35.4 | 35.3 |
| 19 | 4-Cl-φ | H | 73–76 | 10.0 | 10.1 | 44.2 | 42.8 |
| 20 | 4-phenylthio-2-$CH_3$-φ | H | oil | 15.7 | 14.3 | 26.0 | 25.9 |

TABLE I-continued

Compounds of the formula 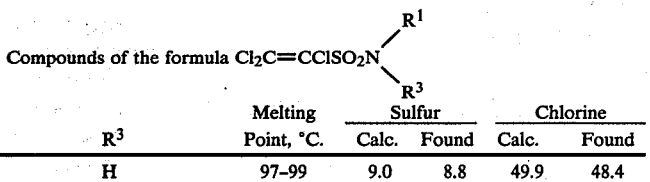

| Compound No. | R[1] | R[3] | Melting Point, °C. | Sulfur Calc. | Sulfur Found | Chlorine Calc. | Chlorine Found |
|---|---|---|---|---|---|---|---|
| 21 | 3,4-Cl$_2$-φ | H | 97–99 | 9.0 | 8.8 | 49.9 | 48.4 |

φ = phenyl

TABLE II

Mycelia Inhibition, micrograms/cm for 99% control

| Compound No. | P | R | A | F |
|---|---|---|---|---|
| 1 | 1.3 | 0.18 | 0.42 | 1.7 |
| 2 | 0.45 | 0.19 | 0.98 | 0.82 |
| 3 | >1.7 | 0.19 | 0.79 | 1.2 |
| 4 | >1.7 | 0.19 | 0.68 | >1.7 |
| 5 | >1.7 | 1.1 | >1.7 | >1.7 |
| 6 | >1.7 | 0.24 | >1.7 | >1.7 |
| 7 | >1.7 | >1.7 | >1.5 | >1.7 |
| 8 | >1.7 | 0.45 | 1.6 | >1.7 |
| 9 | >1.7 | 0.33 | >1.7 | >1.7 |
| 10 | >1.7 | 0.12 | >1.7 | >1.7 |
| 11 | >1.7 | >1.7 | >1.7 | >1.7 |
| 12 | >1.7 | >1.7 | >1.7 | >1.7 |
| 13 | >1.7 | >1.7 | >1.7 | >1.7 |
| 14 | >1.7 | >1.7 | >1.7 | >1.7 |
| 15 | >1.7 | >1.7 | >1.7 | >1.7 |
| 16 | >1.7 | >1.7 | >1.7 | >1.7 |
| 17 | >1.7 | >1.7 | >1.7 | >1.7 |
| 18 | >1.7 | >1.7 | >1.7 | >1.7 |
| 19 | >1.7 | >1.7 | >1.7 | >1.7 |
| 20 | >1.7 | >1.7 | >1.7 | >1.7 |
| 21 | >1.7 | >1.7 | >1.7 | >1.7 |

P = *Pythium ultimum*
R = *Rhizoctonia solani*
A = *Aspergillus niger*
F = *Fusarium moniloforma*

What is claimed is:

1. A compound of the formula

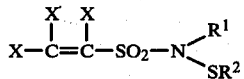

wherein X groups are chloro and bromo, R[1] is alkyl of 1 to 3 carbon atoms, and R[2] is polyhaloalkyl of 1 to 2 carbon atoms and 2 to 5 of the same or different halogen selected from chloro or bromo.

2. The compound of claim 1 wherein the X groups are chloro, R[1] is methyl and R[2] is trichloromethyl.

3. The compound of claim 1 wherein the X groups are chloro, R[1] is methyl and R[2] is 1,1,2,2-tetrachloroethyl.

4. A method of controlling fungi which comprises contacting said fungi with a fungicidally effective amount of a compound of the formula defined in claim 1.

5. The method of claim 4 wherein the X groups are chloro, R[1] is methyl and R[2] is trichloromethyl.

6. The method of claim 4 wherein the X groups are chloro, R[1] is methyl and R[2] is 1,1,2,2-tetrachloroethyl.

7. A fungicidal composition comprising a biologically inert carrier and a fungicidally effective amount of a compound of the formula defined in claim 1.

8. The composition of claim 7 wherein the X groups are chloro, R[1] is methyl and R[2] is trichloromethyl.

9. The composition of claim 7 wherein the X groups are chloro, R[1] is methyl and R[2] is 1,1,2,2-tetrachloroethyl.

* * * * *